United States Patent [19]

Kwan

[11] 4,257,433
[45] Mar. 24, 1981

[54] WATER-DRIVEN TOOTHBRUSH AND WATER-PICK ASSEMBLY

[75] Inventor: Wong K. Kwan, North Point, Hong Kong

[73] Assignee: Well Men Industrial Co. Limited, Quarry Bay, Hong Kong

[21] Appl. No.: 114,195

[22] Filed: Jan. 22, 1980

[51] Int. Cl.³ .......................................... A45D 24/00
[52] U.S. Cl. .................................. 132/11 A; 128/66; 132/84 R
[58] Field of Search ................. 132/11 A; 128/24, 66; 417/440, 38, 414

[56] References Cited

U.S. PATENT DOCUMENTS

| | | | |
|---|---|---|---|
| 3,771,186 | 11/1973 | Morgt | 128/66 |
| 3,809,977 | 5/1974 | Balamuth | 128/66 |
| 3,966,359 | 6/1976 | Woog | 128/66 |

Primary Examiner—G. E. McNeill
Attorney, Agent, or Firm—Perry Carvellas

[57] ABSTRACT

A water-driven toothbrush and water-pick assembly is provided having a housing 1, a handle 3 pivotally attachable to the housing 1 and an elongated toothbrush arm with a brush 41 and water-pick outlet 43 at one end, attachable to the housing also. A water turbine rotor 11 in the housing 1 is connected to the arm 2 via an eccentric link 30 for converting rotary motion of the rotor 11 into agitating pivotal movement of the arm 2 and brush 41. The handle 3 can be pivoted between two positions in one of which water supplied to the handle 3 can be passed to the rotor 11 and exhausted from the handle 3 to actuate the toothbrush arm 2 only to clean a users teeth and in the other of which water supplied to the handle 3 can be passed to the water-pick outlet 43 only to provide a water jet for cleaning crevices between the users teeth.

11 Claims, 13 Drawing Figures

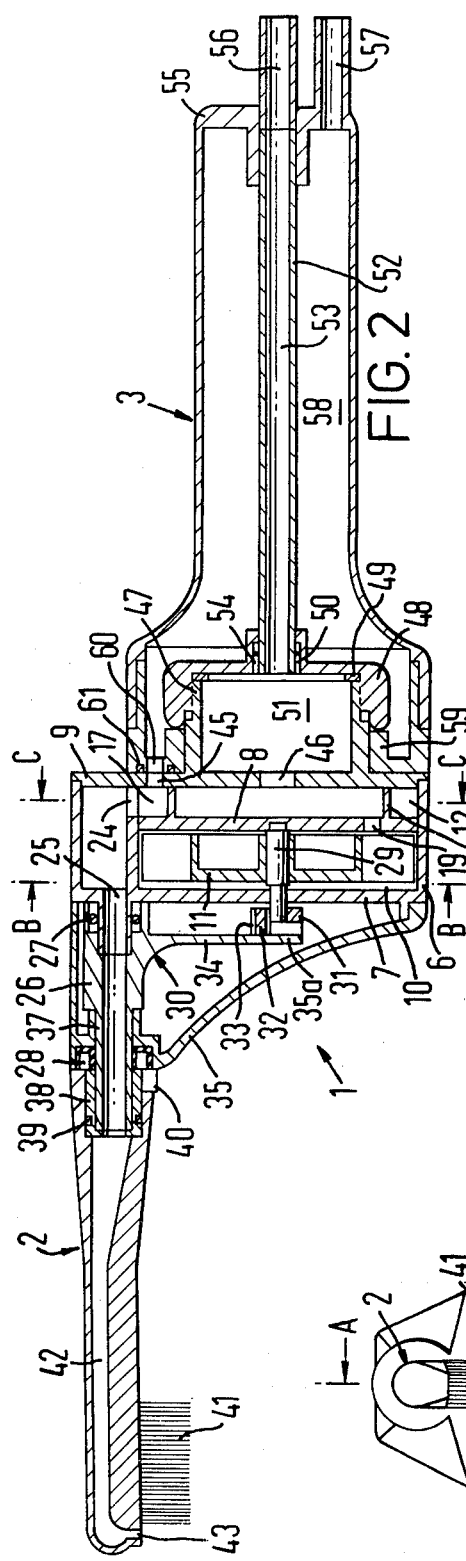

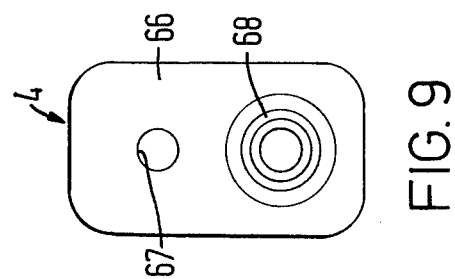
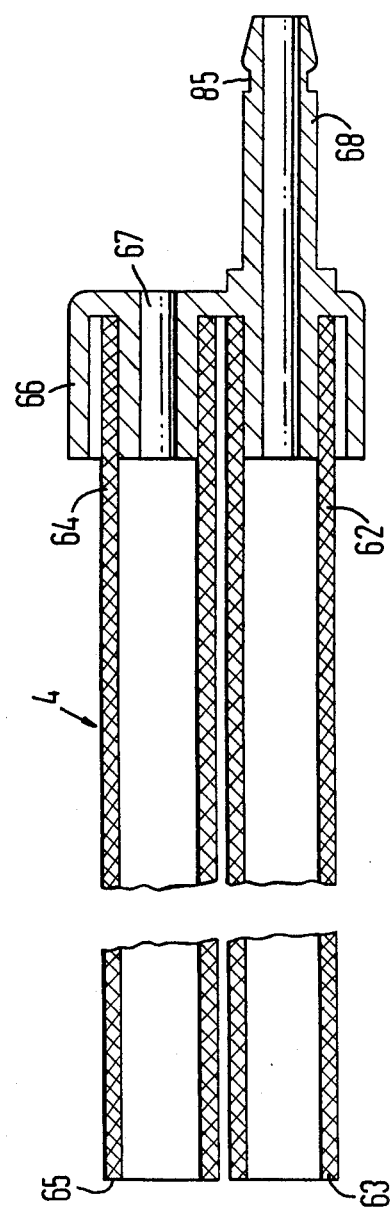
FIG. 9
FIG. 10

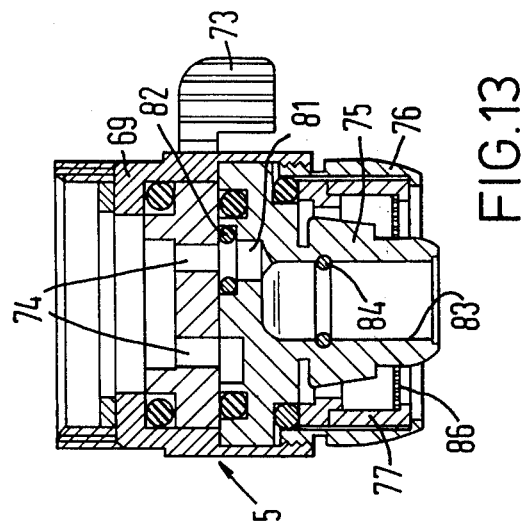
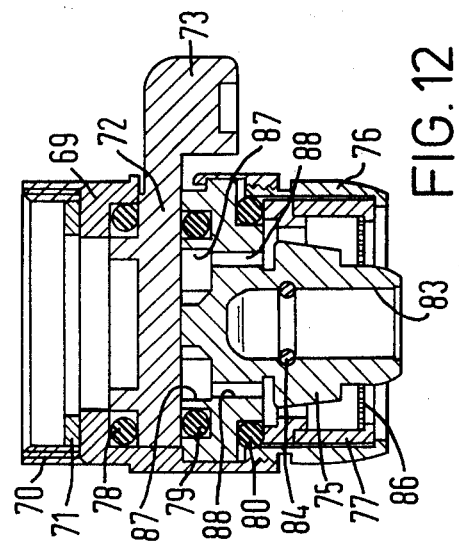
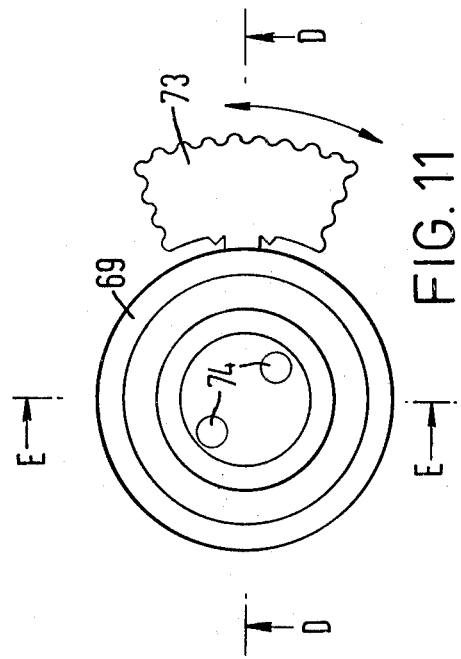

WATER-DRIVEN TOOTHBRUSH AND WATER-PICK ASSEMBLY

FIELD OF THE INVENTION

This invention relates to a water-driven toothbrush and water-pick assembly which makes use of water power either to agitate the toothbrush or to provide a water-pick in the form of a spray of water for cleaning crevices between teeth.

BACKGROUND OF THE INVENTION AND PRIOR ART

Personal hygiene devices in the form of water driven toothbrushes for dental care have been proposed with which a separate toothbrush head or a separate water-pick head can be employed by removing one head and fitting the other in place thereof. This is a time consuming and possibly unpleasant operation which additionally is potentially unhygienic.

OBJECT OF THE INVENTION

An object of the invention is to provide a water-driven toothbrush and water-pick assembly which does not require removal of the toothbrush head to enable a water-pick head to be substituted therefor.

Another object of the invention is to provide a water-driven toothbrush and water-pick assembly with improved hygiene.

SUMMARY OF THE INVENTION

Accordingly the present invention provides a water-driven toothbrush and water-pick assembly, having a housing containing at least two water flow paths, a water turbine rotor located in a first of the at least two water flow paths, a first shaft mounted to pivot about its longitudinal axis, and an eccentric link interconnecting the rotor and first shaft for converting rotary movement of the rotor into pivotal movement of the first shaft, an elongated toothbrush arm for mounting a toothbrush head, which arm contains a water passage extending from a water-pick outlet adjacent the head end of the arm to the other end of the arm and is fixedly connectible at the other end of the arm to the first shaft for pivotal agitation therewith and to form part of a second of the at least two water flow paths, and a handle containing a water inlet passage connectible to a source of water under gravity or pressure, and a water outlet passage, which handle is mountable on the housing for pivotal movement between at least first and second positions, so that when the water inlet passage is operatively connected to a source of water the handle can be pivoted into and out of the first position in which the water passes through the water inlet passage, along the first water flow path to rotate the turbine rotor and thereby pivotally agitate the toothbrush arm and head, and exit through the water outlet passage without actuating the water-pick, and into and out of the second position in which the water passes through the water inlet passage, the second water flow path, along the arm water passage and out of the water-pick outlet without actuating the toothbrush arm.

Preferably, the housing has a hollow cylindrical body portion radially subdivided internally by axially spaced first, second and third partition walls into a stator chamber containing the rotor and located between the first and second partition walls, and a second chamber located between the second and third partition walls, which second chamber is subdivided by walls into first and second separate part-annular outer passages and an inner cylindrical chamber which communicates via an aperture through the second partition wall with the stator chamber, and wherein the housing has, on the outer periphery of the body portion, a first external chamber communicating with the first part-annular outer passage and with the stator chamber, and a second external chamber communicating with the second part-annular outer passage, the first part-annular outer passage, first external chamber, stator chamber and inner cylindrical chamber forming part of the first water flow path and the second part-annular outer passage and second external chamber forming part of the second water flow path.

Advantageously the third partition wall has a first aperture therethrough communicating with the first part-annular outer passage, a second aperture therethrough communicating with the second part-annular outer passage and a third aperture therethrough communicating with the inner cylindrical chamber.

Additionally the handle is pivotally attached to the third partition wall of the housing with the third aperture of the third partition wall communicating with the water outlet passage and with a movable opening in the handle communicating with the water inlet passage, the movable opening being located and dimensioned such that when the handle is in the first position the movable opening communicates with the first part-annular outer passage and when the handle is in the second position the movable opening communicates with the second part-annular outer passage.

The assembly advantageously may include an elongated flexible conduit means for attachment to the handle and to a source of water with or without the interposition of a tap means operable to control the supply of water to the conduit means.

Other objects and features of the invention will become apparent from the following detailed description of a preferred but non-limitative embodiment and the accompanying drawings made a part hereof and to which reference is made.

BRIEF DESCRIPTION OF THE DRAWINGS

FIG. 1 is a front end view of water-driven toothbrush and water-pick assembly according to one embodiment of the invention, FIG. 2 is longitudinal sectional view taken on the line A—A of FIG. 2, FIG. 3 is a transverse sectional view taken on the line B—B of FIG. 2 but shown in full, FIG. 4 is a transverse sectional view taken on the line C—C in FIG. 3 but shown in full, FIG. 5 is a rear end view of the assembly of FIGS. 1 to 4, FIG. 9 is a rear end view of a conduit means of the assembly of FIGS. 1 to 8, FIG. 10 is longitudinal sectional view of the conduit means of FIG. 9, FIG. 11 is a plan view from above of a tap means of the assembly of FIGS. 1 to 10, FIG. 12 is a vertical axial section taken on the line D—D of FIG. 11, in one position, and FIG. 13 is a vertical axial section taken on the line E—E of FIG. 11, in another operative position.

Figure 6:
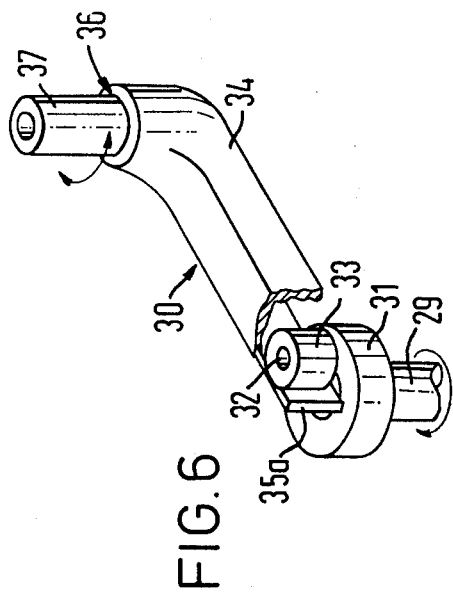
FIG. 6 is a perspective view to an enlarged scale of a feature of the assembly of FIGS. 1 to 5, with parts broken away for clarity.
Figure 7:
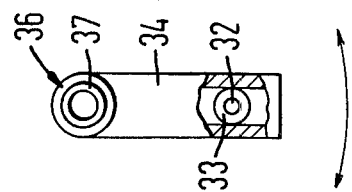
FIG. 7 is a plan part-sectional view of the feature of FIG. 6.

As shown in the accompanying drawings a water-driven toothbrush and water-pick assembly according to one embodiment of the invention includes a housing 1, an elongated toothbrush arm 2 and a handle 3 with or without optional elongated flexible conduit means 4 and tap means 5 for connecting the handle 3 to a source of water under gravity or pressure. The housing 1, as shown in FIGS. 1 to 5, has a hollow cylindrical body portion 6, contains at least two water flow paths, and is made of any convenient material such as plastics.

The body portion 6 is radially subdivided internally by axially spaced first, second and third partition walls 7, 8 and 9 respectively, into a stator chamber 10 containing a water turbine rotor 11, located between the first partition wall 7 and the second partition wall 8, and into a second chamber 12 located between the second partition wall 8 and the third partition wall 9. This second chamber 12 is further subdivided by walls 13, 14 and 15 into a first part-annular outer passage 16, a separate second part-annular outer passage 17 and an inner cylindrical chamber 18. The walls 14 and 15 are located to one side of a vertical diameter through the chamber 12, as shown in FIG. 4, so that the part-annular passage 17 is larger than the part-annular passage 16, for reasons which will later become apparent.

The stator chamber 10 communicates via an aperture 19 through the second partition wall 8 near the base of the chamber 10, with the inner cylindrical chamber 18. The housing 1 has on the outer periphery of the body portion 6, a first external chamber 20 and a second external chamber 21. The first external chamber 20 communicates with the first part-annular outer passage 16 via an opening 22 at one end of the chamber 20 and with the stator chamber 10, which it overlies, via an opening 23 (shown in FIG. 3) at the opposite end of the chamber 20. This first part-annular outer passage 16, the first external chamber 20, the stator chamber 10 and the inner cylindrical chamber 18 form part of the first water flow path.

The second external chamber 21 communicates with the second part-annular outer passage 17 via an opening 24 at one end of the chamber 21 and at the other end communicates via an opening 25 with an open end of an elongated hollow first shaft 26 mounted for pivotal movement about its longitudinal axis in journals sealed by rubber or plastics 'O' or 'D' rings 27 and 28 in the housing 1. The second part-annular outer passage 17, the second external chamber 21, the opening 25 and the hollow interior of the first shaft 26 form part of the second water flow path.

Figure 8:
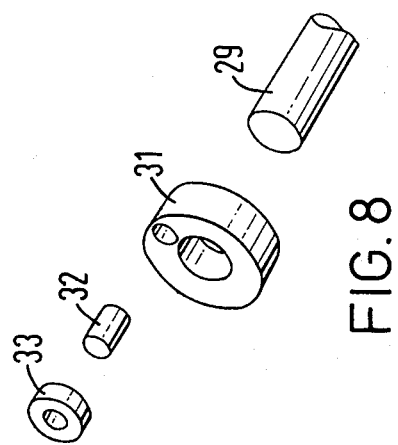
FIG. 8 is an exploded view of a detail of the feature of FIGS. 6 and 7 to a larger scale.

The turbine rotor 11, conveniently made of plastics material, is fixedly mounted on a rotor shaft 29 rotatably journalled at one end in the second partition wall 8. The other end of the shaft 29 projects through, and is supported by, the first partition wall 7, and carries an eccentric link generally indicated at 30 in FIGS. 2 and 6. This eccentric link 30 includes a ring 31 (see FIGS. 2, 6 and 8) fixed to the end of the rotor shaft 29, which shaft and ring can be made of any convenient material such as metal or plastics. A pin 32 projects from an annular outer face of the ring 31 at an axial spacing from the rotational axis of the rotor shaft 29 and a cam disc 33 is rotatably mounted on the pin 32. A link arm 34 of generally U-shaped cross-section is mounted in a housing portion 35 with one open end 35a of the arm 34 slidably fitted over the cam disc 33, thereby retaining it on the pin 32, and with the other end 36 of the arm 34 being fixedly connected to or forming part of the first shaft 26. This eccentric link 30 converts rotary movement of the rotor 11 and shaft 29 into pivotal reciprocating movement of the shaft 26.

Conveniently as shown in FIG. 2, the other end of the shaft 26 and has a reduced diameter portion 37 which projects from the housing 1 through the seal ring 28. The end of this shaft portion 37 projecting from the housing 1 is releasably fixedly engageable with the toothbrush arm 2 via an apertured end cap 38, rubber sealing ring 39 and locking key 40, so that the arm reciprocatingly pivots about its longitudinal axis with the shaft 26.

The elongated toothbrush arm 2 carries a fixed or removable toothbrush head 41 adjacent its outer most end and has a water passage 42 extending therethrough from a water-pick outlet 43 at the head end of the arm to the other end of the arm 2 which is connectible to the shaft portion 37 projecting from the housing 1. This water passage 42 communicates at the end of the shaft portion 37 with the hollow interior of the shaft 26 which interior is in communication with the second external chamber 21 via the opening 25. The outlet 43, passage 42 and hollow interior of the shaft 26 thus form part of the second water flow path.

At the other end of the housing 1, the third partition wall 9 has a first aperture 44 (not shown) therethrough communicating with the first part-annular outer passage 16, a second aperture 45 therethrough communicating with the second part-annular outer passage 17 and a third aperture 46 therethrough communicating with the inner cylindrical chamber 18. The wall 9 is provided externally with a projecting reduced diameter stepped annular shoulder 47 to which the handle 3 is pivotally attached. To this end the outer end of the shoulder 47 is externally screw-threaded for engagement by a corresponding screw-thread provided on the interior of a lock-nut 48. This lock-nut 48 fits over the open end of the shoulder 47 with the interposition therebetween of a sealing ring 49 and has a central aperture 50 therethrough communicating with a chamber 51 formed by the interior of the shoulder 47, which chamber 51 communicates via the aperture 46 with the inner cylindrical chamber 18.

The handle 3 has an axial central tube 52 providing a water outlet passage 53 therethrough, which tube 52 fits rotatably at one end into the aperture 50 of the lock-nut 48 with the interposition therebetween of a rubber sealing ring 54, so that the open end of the passage 53 communicates with the chamber 51. At the opposite end the tube 52 is attached to an end plate 55 of the handle 3 in communication with an outlet tube 56 connectible to a receptacle as desired to receive waste water emitted from the passage 53.

The handle 3 is hollow and the end plate 55 is provided also with a water inlet tube 57 attachable to a source of water under gravity or pressure. This tube 57 communicates with the interior of the handle 3 which thus constitutes a water inlet passage 58 separate from the outlet passage 53. The forward end of the handle 3 remote from the end plate 55 has a diameter and shape such as to fit pivotably over the shoulder 47 and be retained there on by the lock-nut 48 in sliding contact with the outer surface of the third partition wall 9. To this end the handle 3 is provided with an annular ring portion 59 having an outer diameter conforming to that of the forward end of the handle 3 to which it is attached in any convenient way, such as by adhesive.

The inner diameter of the ring portion 59 is such as to be a sliding rotatable fit on the outside of the larger diameter portion of the shoulder 47 where it is retained by the lock-nut 48 against the outer end surface of the third partition wall 9. In this way the handle 3 is pivotally mounted on the housing 1 for limited pivotal movement about its longitudinal axis about the shoulder 47. An opening 60 is provided through the ring portion 59 which opening 60 is sealed by a seal ring 61 against the outer end surface of the third partition wall 9. This opening 60 is dimensioned and located so that when the handle 3 is pivoted into a first position the opening 60 is aligned with the opening 44 and hence the first part-annular chamber 13 allowing water to pass from the source, through the handle inlet passage 58 and through the first water flow path to drive the turbine rotor 11 and thus agitate the toothbrush arm 2 and toothbrush head 41 for teeth brushing purposes. That is to say the water flows through the inlet 57, along the passage 58, through the opening 60 and aligned opening 44 (not shown), into the first part-annular outer chamber 16, through the opening 22, the chamber 20, the opening 23, over and so rotating the rotor 11 in the chamber 10, through aperture 19, chamber 18, aperture 46, chamber 51, passage 53 and out of the handle at outlet 56. Rotary motion of the rotor 11 causes pivotal reciprocating movement of the shaft 26 and attached arm 2 as rotational movement of the ring 31 is converted into pivotal movement of the link arm 34 about the longitudinal axis of the shaft 26. The arm 2 and thus the head 41 is thereby pivotally agitated to a limited extent about the longitudinal axis of the arm 2.

In this first position of the handle 3 water is supplied only to the turbine rotor 11 to drive the toothbrush head 41 only and no water is supplied to the water-pick outlet 43. To actuate the water-pick the handle 3 is pivoted about its longitudinal axis to a second position in which the water flow is cut-off from the first water flow path and passed into the second water flow path only. In the handle second position the opening 60 is moved out of communication with the aperture 44 and into communication with the aperture 45. In this position the water flows from passage 58, through opening 60, opening 45, chamber 17, opening 24 chamber 21, opening 25, interior of shaft 26, along passage 42 and out of the outlet 43 in a jet-spray for insertion in a users mouth to act as a water-pick for cleaning crevices between the teeth. In this instance water issuing from the outlet 43 is returned to waste from the users mouth only.

The assembly of the invention advantageously also includes elongated flexible conduit means generally referenced 4 in FIGS. 9 and 10. The means 9 includes a water outlet conduit 62 releasably attachable at one end 63 to the outlet 56 of the handle end plate 55, such as being a push fit over the outlet 56. The means 4 also includes a water inlet conduit 64 releasably attachable at one end 65 to the water inlet 57 on the handle end plate 55. The conduits 62 and 64 at their other ends are fitted to an end plate 66. This end plate provides an outlet aperture 64 for the conduit 64 and an apertured shaped inlet nozzle 68 for the conduit 62, for attachment to a source of water under gravity or other pressure.

Conveniently the inlet nozzle 68 is attachable to a source of water, via the tap means 5 shown in FIGS. 11 to 13. This tap means 5 has a body 69 of generally cylindrical shape and made of any convenient material such as plastics material. The body 69 has an open necked inlet portion 70 at one end with an inner and outer threaded portions whereby it can be releasably attached to the outlet of a water tap. A rubber washer 71 is located on a shoulder within the necked portion 70 to abut sealingly against the end of a water tap when introduced into the necked portion. The body portion 69 is axially bored and provided with a valve in the form of a switch plate 72 with an external acuating lever 73 for pivotally moving the plate 72 about the longitudinal axis of the means 5 between two limit positions.

This plate 72 is provided with one or more apertures 74 therethrough and co-operates with a fixed water separator 75 housed within the body portion 69 and held therein by a screw threaded outlet ring 76 and inner spacer ring 77 releasably screwed in the end of the body portion 69 remote from the necked portion 70. Ring seals 78, 79 and 80 respectively, conveniently made of rubber, are located respectively between the body portion shoulder and switch plate 72, between the switch plate 72 and water separator 75 and between the water separator 75 and the inner spacer ring 77. In a first limit position of the switch plate 72 the necked inlet portion 70 is put in communication via the apertures 74 with an aperture 81 in the switch plate 75, sealed by a rubber ring 82, and an inner outlet passage 83 opening through one end of the water separator 75. The passage 83 is provided with an internal rubber sealing ring 84 housed in an annular recess to engage with a corresponding annular groove 85 in the inlet nozzle 68 which is a push fit in the passage 83 and releasably retained therein by engagement with the ring 84. Thus water can be passed into the conduit 62 via the passage 83 and nozzle 68.

In the second limit position of the switch plate 72 the necked inlet portion 70 is put in communication with a meshed water by-pass outlet 86 via the apertures 74 and apertures 87 and 88, so that water can pass from the inlet portion 70 and out of the meshed water by-pass outlet 86 without passing through the passage 83. This is useful to allow a water tap fitted with the assembly of the invention to be used separately from the assembly and without disconnecting the assembly therefrom.

We claim:

1. A water-driven toothbrush and water-pick assembly having a housing containing at least two water flow paths, a water turbine rotor located in a first of the at least two water flow paths, a first shaft mounted to pivot about its longitudinal axis, and an eccentric link interconnecting the rotor and first shaft for converting rotary movement of the rotor into pivotal movement of the first shaft, an elongated toothbrush arm for mounting a toothbrush head, which arm contains a water passage extending from a water-pick outlet adjacent the head end of the arm to the other end of the arm and is fixedly connectible at the other end of the arm to the first shaft for pivotal agitation therewith and to form part of a second of the at least two water flow paths, and a handle containing a water inlet passage connectible to a source of water under gravity or pressure, and a water outlet passage, which handle is mountable on the housing for pivotal movement between at least first and second positions, so that when the water inlet passage is operatively connected to a source of water the handle can be pivoted into and out of the first position in which the water passes through the water inlet passage, along the first water flow path to rotate the turbine rotor and thereby pivotally agitate the toothbrush arm and head, and exit through the water outlet passage without actuating the water-pick, and into and out of the second position in which the water passes through the water inlet passage, the second water flow path, along the arm water passage and out of the water-pick outlet without actuating the toothbrush arm.

2. An assembly according to claim 1, wherein the housing has a hollow cylindrical body portion radially subdivided internally by axially spaced first, second and third partition walls into a stator chamber containing the rotor and located between the first and second partition walls, and a second chamber located between the second and third partition walls, which second chamber is subdivided by walls into first and second separate part-annular outer passages and an inner cylindrical chamber which communicates via an aperture through the second partition wall with the stator chamber, and wherein the housing has on the outer periphery of the body portion, a first external chamber communicating with the first part-annular outer passage and with the stator chamber, and a second external chamber communicating with the second part-annular outer passage, the first part-annular outer passage, first external chamber, stator chamber and inner cylindrical chamber forming part of the first water flow path and the second part-annular outer passage and second external chamber forming part of the second water flow path.

3. An assembly according to claim 2, wherein the rotor is fixedly mounted on a rotor shaft rotatably supported at one end in the second partition wall and carries at the other end, which extends through the first partition wall, the eccentric link.

4. An assembly according to claim 3, wherein the eccentric link includes a ring fixed to the other end of the rotor shaft, a pin projecting from an annular outer face of the ring and axially spaced from the rotational axis of the rotor shaft, a cam disc rotatably mounted on the pin, and a link arm of generally U-shaped cross-section, one end of which is slidably fitted over the cam disc and the other end of which is fixedly connected to or forms part of the first shaft.

5. An assembly according to claim 4 wherein the first shaft is hollow, forms part of the second water flow path and is pivotally mounted in the housing adjacent the first and second external chambers in communication at one end with the second external chamber.

6. An assembly according to claim 5, wherein the other end of the first shaft projects from the housing for releasably fixed engagement with the toothbrush arm and communication with the arm water passage.

7. An assembly according to claim 6, wherein the toothbrush arm end fits over the other end of the first shaft and is releasably fixed thereto by a locking key.

8. An assembly according to claim 7, wherein the third partition wall has a first aperture therethrough communicating with the first part-annular outer passage, a second aperture therethrough communicating with the second part-annular outer passage and a third aperture therethrough communicating with the inner cylindrical chamber.

9. An assembly according to claim 8, wherein the handle is pivotally attached to the third partition wall of the housing with the third aperture of the third partition wall communicating with the water outlet passage and with a movable opening in the handle communicating with the water inlet passage, the movable opening being located and dimensioned such that when the handle is in the first position the movable opening communicates with the first part-annular outer passage and when the handle is in the second position the movable opening communicates with the second part-annular outer passage.

10. An assembly according to claim 9, including elongated flexible conduit means in the form of a water outlet conduit releasably attachable to the handle water outlet passage to lead the water to a receptacle, and a water inlet conduit releasably attachable at one end to the handle water inlet passage and at the other end to a source of water.

11. An assembly according to claim 10, including a tap means releasably connectible at one end to a source of water and at the other end to the other end of the water inlet conduit, the tap means incorporating a valve operable to allow the passage of water from the source either to the water inlet conduit or to a by-pass outlet.

* * * * *